(12) United States Patent
Egashira

(10) Patent No.: US 8,337,896 B2
(45) Date of Patent: Dec. 25, 2012

(54) DRUG-CONTAINING NANOPARTICLES

(75) Inventor: Kensuke Egashira, Fukuoka (JP)

(73) Assignees: Kyushu University, National University Corporation, Fukuoka (JP); Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/735,035

(22) PCT Filed: Dec. 12, 2008

(86) PCT No.: PCT/JP2008/073139
§ 371 (c)(1),
(2), (4) Date: Aug. 27, 2010

(87) PCT Pub. No.: WO2009/075391
PCT Pub. Date: Jun. 18, 2009

(65) Prior Publication Data
US 2010/0331373 A1   Dec. 30, 2010

(30) Foreign Application Priority Data

Dec. 13, 2007   (JP) ................................. 2007-322409
May 12, 2008   (JP) ................................. 2008-125071

(51) Int. Cl.
*A61K 9/14*   (2006.01)
*A61K 9/00*   (2006.01)
(52) U.S. Cl. .......................... 424/489; 424/422; 424/497
(58) Field of Classification Search .......................... None
See application file for complete search history.

(56) References Cited

U.S. PATENT DOCUMENTS

| | | | |
|---|---|---|---|
| 7,223,728 B2 * | 5/2007 | Yakubu-Madus et al. | 514/6.8 |
| 2004/0077689 A1 | 4/2004 | Sugiyama et al. | |
| 2004/0219208 A1 | 11/2004 | Kawamura et al. | |
| 2005/0095267 A1 * | 5/2005 | Campbell et al. | 424/425 |
| 2006/0045901 A1 | 3/2006 | Weber | |
| 2006/0210604 A1 * | 9/2006 | Dadey et al. | 424/427 |
| 2007/0098802 A1 * | 5/2007 | Farr et al. | 424/489 |
| 2008/0020014 A1 * | 1/2008 | Consigny et al. | 424/423 |
| 2008/0026040 A1 * | 1/2008 | Farr et al. | 424/443 |

FOREIGN PATENT DOCUMENTS

| | | |
|---|---|---|
| JP | 2007-119396 A | 5/2007 |
| JP | 2007-215620 A | 8/2007 |
| WO | WO 99/25346 A1 | 5/1999 |
| WO | WO 02/087580 A1 | 7/2002 |
| WO | WO 2008/124632 A1 | 10/2008 |

OTHER PUBLICATIONS

In: Biological and Biomedical Coating Handbook: Applicatiohns (Edited by Sam Zhang Edited by Sam Zhang). Tang, J.Zh. and Rhodes, N.P. Release-controlled coatings. Chapter 6, p. 259-300, 2010 (review).*
Rodriguez, A.E. Emerging drugs for coronary restenosis: the role of systemic oral agents in the stent era. Expert Opin. Emerging Drugs (2009) 14(4):561-576 (review).*
Koga et al., "Monocyte-targeting Nanoparticle-based Delivery of Pioglitazone Inhibits Plaque Rupture in the Branchiocephalic Arteries of Apolipoprotein-E Deficient Mice," Circulation Journal, Mar. 1, 2008, 72(Suppl 1):227, Abstract OE-188.
International Search Report mailed Apr. 15, 2009, in PCT/JP2008/073139, 4 pages.
Huang et al., "Pioglitazone ameliorates endothelial dysfunction and restores ischemia-induced angiogenesis in diabetic mice," Biomedicine & Pharmacotherapy, 2008, 62:46-52.
Matoba et al., "Nanoparticle-based Monocyte-Selective Delivery of PPARγ Agonist Pioglitazone Inhibits Plaque Rupture in ApoE-Deficient Mice," Circulation, Oct. 28, 2008, 118(18)Supp2:S449-S450, Abstract 3605.
Sasaki et al., "Oral Anti-CD3 Antibody Treatment Induces CD4+Lap+ Regulatory T Cells and Ameliorates the Development of Atherosclerosis in Mice," Circulation Journal, Mar. 1, 2008, 72,Suppl :227, Abstract OE-189.
Soppimath et al., "Biodegradable polymeric nanoparticles as drug delivery devices," Journal of Controlled Release, Jan. 29, 2001, 70(1-2):1-20.

* cited by examiner

*Primary Examiner* — Robert A Wax
*Assistant Examiner* — Olga V Tcherkasskaya
(74) *Attorney, Agent, or Firm* — Foley & Lardner LLP

(57) ABSTRACT

The present invention relates to nanoparticles containing pioglitazone or a salt thereof and a biocompatible polymer, a pharmaceutical preparation containing the nanoparticles for the prophylaxis or treatment of arteriosclerotic diseases, and a stent carrying the nanoparticles. Using the nanoparticles of the present invention, rupture of arteriosclerotic plaque can be suppressed, and they are useful for the prophylaxis or treatment of arteriosclerotic diseases.

12 Claims, No Drawings

DRUG-CONTAINING NANOPARTICLES

TECHNICAL FIELD

The present invention relates to nanoparticles containing pioglitazone or a salt thereof, and a pharmaceutical preparation and a stent containing the same.

BACKGROUND OF THE INVENTION

With the advancement of the coronary intervention (Percutaneous coronary intervention; PCI) technique including a drug eluting stent (DES), post-PCI restenosis, which has conventionally been an issue of concern, has decreased. However, DES currently used in the world contains an immunosuppressant (e.g., sirolimus) or an anticancer agent (e.g., paclitaxel) and, as compared to conventional bare metal stents (BMS), DES has been reported to show, though it can suppress restenosis, higher incidence of acute coronary syndrome (ACS) in long-term prognosis, which is a fatal pathology, than BMS, and also clarified to not improve vital prognosis.

The presumed reason therefor is that, although acute coronary syndrome is mostly caused by rupture of arteriosclerotic plaque (plaque rupture), which is a comparatively mild to moderate lesion, rather than a severe stenotic lesion, which is conventionally the target of PCI, DES using an immunosuppressant or anticancer agent suppresses restenosis by suppressing neointimal thickening via prevention of smooth muscle cell growth, and its non-specific cell proliferation suppressive action prevents vascular endothelial regeneration and forms unstable plaque that becomes thrombus, thus increasing the incidence of ACS.

For improvement of vital prognosis, therefore, prevention of plaque rupture that causes acute coronary syndrome is important, and the development of a stent having a neointimal thickening suppressive action as well as a plaque stabilizing action by not preventing vascular endothelial regeneration and the like is considered to be an effective therapeutic strategy.

Peroxisome proliferator-activated receptor (PPAR) is a nuclear receptor which is activated by a ligand and functions as a transcription factor. PPAR has subtypes of $\alpha$, $\gamma$ and $\beta/\delta$, and is deeply involved in the metabolism of carbohydrate, lipid and the like, and cell differentiation. PPAR$\gamma$ is known to be expressed on vascular endothelial cell, vascular smooth muscle cell, macrophage and T lymphocyte in arteriosclerotic lesion.

In arteriosclerosis, PPAR$\gamma$ agonists are considered to afford an anti-arteriosclerotic action by direct actions such as
  protection and improvement of endothelial function by, for example, suppression of expression of adhesion factors such as ICAM-1, VCAM-1 and the like in endothelial cells, and the like
  suppression of migration and growth of smooth muscle cells and MMP (matrix metalloproteinase) production in smooth muscle cells
  suppression of monocyte differentiation and inflammatory cytokine production
  promotion of reverse cholesterol transport mediated by ABCA1 in macrophages and the like.

Pioglitazone, which is an insulin sensitizer, has a PPAR$\gamma$ agonist action and an apoptosis suppressive action, and is known to be useful for the treatment of atherosclerotic diseases, the prophylaxis or treatment of vascular reocclusion and restenosis after bypass operation and the prophylaxis or treatment of vascular thickening after intervention (percutaneous transluminal coronary angioplasty, percutaneous coronary revascularization, stenting, coronary endoscopy, intravascular sonication, percutaneous transluminal coronary thrombolytic therapy etc.) (WO99/25346, WO02/087580 etc.).

As a drug delivery system, moreover, nanoparticles encapsulating a nucleic acid compound (JP-A-2007-119396) and a drug eluting stent coated with nanoparticles encapsulating a physiologically active substance (JP-A-2007-215620) are known.

DISCLOSURE OF THE INVENTION

It is expected that selective delivery of PPAR$\gamma$ agonists to unstable plaques will prevent plaque rupture and subsequent acute coronary syndrome, and improve vital prognosis.

However, a glitazone drug having a PPAR$\gamma$ agonist action is known to possibly cause edema as a side effect of systemic administration (oral administration).

Accordingly, efficient delivery of a small amount of a drug to a target organ (blood vessel) using a drug delivery system (DDS) may minimize systemic side effects and provide a promising treatment even for patients for whom glitazone drugs are unusable.

The present invention aims to provide a novel pharmaceutical preparation useful for the prophylaxis or treatment of arteriosclerotic diseases.

The present inventor has found that pioglitazone, which is a PPAR$\gamma$ agonist, or a salt thereof can be efficiently delivered to an unstable plaque by using nanoparticles containing pioglitazone or a salt thereof to suppress occurrence of plaque rupture, and can be a pharmaceutical preparation useful for the prophylaxis or treatment of arteriosclerotic diseases.

Accordingly, the present invention relates to
(1) a nanoparticle comprising pioglitazone or a salt thereof and a biocompatible polymer;
(2) the nanoparticle of the aforementioned (1), wherein the biocompatible polymer is a lactic acid-glycolic acid copolymer;
(3) the nanoparticle of the aforementioned (1), wherein the content of pioglitazone or a salt thereof is 0.1 to 10 wt % as pioglitazone;
(4) the nanoparticle of the aforementioned (1), which is used for the prophylaxis or treatment of arteriosclerotic diseases;
(5) the nanoparticle of the aforementioned (4), which is used for parenteral administration;
(6) a pharmaceutical preparation comprising the nanoparticle of the aforementioned (1), which is used for the prophylaxis or treatment of arteriosclerotic diseases;
(7) a pharmaceutical preparation for parenteral administration, comprising the nanoparticle of the aforementioned (1), which is used for the prophylaxis or treatment of arteriosclerotic diseases;
(8) a stent carrying the nanoparticle of the aforementioned (1);
(9) a stent carrying the nanoparticle of the aforementioned (1), which is used for the prophylaxis or treatment of arteriosclerotic diseases;
(10) a method for the prophylaxis or treatment of an arteriosclerotic disease in a mammal, comprising administering an effective amount of the nanoparticle of the aforementioned (1) to the mammal;
(11) use of the nanoparticle of the aforementioned (1) for the production of a pharmaceutical agent for the prophylaxis or treatment of arteriosclerotic diseases;

(12) a method for the prophylaxis or treatment of an arteriosclerotic disease in a mammal, comprising placing the stent of the aforementioned (8) in a blood vessel of the mammal;
(13) use of the nanoparticle of the aforementioned (1) for the production of a stent for the prophylaxis or treatment of arteriosclerotic diseases, and the like.

In addition, the present invention relates to
(14) the nanoparticle of the aforementioned (1), further comprising a cationic polymer;
(15) the nanoparticle of the aforementioned (14), wherein the cationic polymer is chitosan;
(16) a stent carrying the nanoparticle of the aforementioned (14);
(17) a stent carrying the nanoparticle of the aforementioned (14), which is used for the prophylaxis or treatment of arteriosclerotic diseases, and the like.

The nanoparticle of the present invention has an action to suppress occurrence of plaque rupture by efficiently delivering pioglitazone or a salt thereof to an unstable plaque, as well as a stable long-term retention action at a vascular lesion site, and a suppressive action on neointimal formation after vascular injury. Therefore, the nanoparticle of the present invention can be used for the prophylaxis or treatment of arteriosclerotic diseases, in-stent restenosis and the like. Using the nanoparticle of the present invention, a small amount of a drug can be efficiently delivered to a target organ (blood vessel), which enables reduction of systemic side effects. In addition, since a drug can be gradually released from the nanoparticle, a pharmaceutical preparation superior in the sustainability can be provided.

In leg ischemia, PPARγ agonists are considered to exhibit an angiogenesis action in an ischemic tissue by a direct action such as an endothelial function protecting-improving effect by promoted expression of eNOS in endothelial cells.

The nanoparticle of the present invention has an action to improve and protect endothelial functions by specifically and efficiently delivering pioglitazone or a salt thereof to vascular endothelial cells in an ischemic site. The action mechanism thereof is considered to be based on a promoted expression of eNOS. Accordingly, the nanoparticles of the present invention can be used for the treatment of ischemic diseases. Using the nanoparticles of the present invention, a small amount of a drug can be efficiently delivered to an ischemic organ (vascular endothelial cell), which enables reduction of systemic side effects. Moreover, since a drug can be gradually released from the nanoparticle, a pharmaceutical preparation superior in the sustainability can be provided.

Furthermore, the pharmaceutical preparation and stent of the present invention also have an action to suppress occurrence of plaque rupture. Accordingly, they can be used for the prophylaxis or treatment of arteriosclerotic diseases, in-stent restenosis and the like.

Particularly, a stent carrying the nanoparticle of the present invention has an action to suppress neointimal formation after stenting, and is useful for the prophylaxis or treatment of arteriosclerotic diseases, in-stent restenosis and the like.

Furthermore, the nanoparticle, pharmaceutical preparation and stent of the present invention also have an action to suppress production of monocyte chemotactic factor (MCP-1). Accordingly, they can be used for the prophylaxis or treatment of diseases involving MCP-1, for example, for the prophylaxis or treatment of inflammatory diseases.

DETAILED DESCRIPTION OF THE INVENTION

The nanoparticle of the present invention comprises pioglitazone or a salt thereof and a biocompatible polymer, and is formed as a particle (nanosphere) with a nano-size.

While the production method of the nanoparticle of the present invention is not particularly limited as long as it can process pioglitazone or a salt thereof and a biocompatible polymer to particles having an average particle size of less than 1,000 nm, a spherical crystallization method, which is a non-high shearing force particle preparation method, can be preferably used.

The spherical crystallization method is a method that designs spherical crystal particles by controlling the formation/growth process of the crystal in the final process of compound synthesis, and processes the particles by directly controlling the property thereof. One of the spherical crystallization methods is an emulsion solvent diffusion method (ESD method).

The ESD method is a technique that produces nanosphere by the following principles. In this method, two kinds of solvents are used: a good solvent that can dissolve a lactic acid-glycolic acid copolymer (hereinafter to be referred to as PLGA) and the like, to be a base polymer containing a drug, and a poor solvent that conversely does not dissolve PLGA. As the good solvent, an organic solvent such as acetone and the like, which dissolves PLGA and is miscible with a poor solvent. As the poor solvent, an aqueous solution of polyvinyl alcohol and the like are generally used.

As the operational step, PLGA is first dissolved in a good solvent, and a drug solution is added to and mixed with the good solvent while preventing precipitation of PLGA. The obtained mixture containing PLGA and the drug is added dropwise to a poor solvent with stirring. As a result, the good solvent (organic solvent) in the mixture is rapidly diffused and transferred into a poor solvent, which in turn causes self-emulsification of the good solvent in the poor solvent, forming an emulsion droplet of the good solvent with a submicron size. Furthermore, since the organic solvent in the emulsion continuously diffuses into the poor solvent due to mutual diffusion of the good solvent and the poor solvent, the solubility of PLGA and the drug in the emulsion droplet decreases, and finally, PLGA nanosphere of spherical crystal particles containing the drug is produced.

According to the above-mentioned spherical crystallization method, since nanoparticles can be formed by a physicochemical method and the obtained nanoparticles are substantially spherical, uniform nanoparticles can be formed easily without the need to consider the problems of residual catalyst and starting material compound. Thereafter, the organic solvent (good solvent) is evaporated under reduced pressure (solvent evaporation step) to give a drug-containing nanoparticle powder. The obtained powder is directly or, where necessary, after formation of composite (composite forming step) by freeze-drying and the like into redispersible aggregated particles (composite particles) and filled in a container.

The kind of the good solvent and poor solvent is determined according to the drug to be contained in nanoparticles, the kind of biocompatible polymer, and the like, and is not particularly limited. Since biocompatible nanoparticle is used as a starting material of a pharmaceutical preparation to be acted on the human body, one having high safety to the human body and posing a less environmental load needs to be used.

Examples of such poor solvent include water and water added with a surfactant and, for example, an aqueous solution of polyvinyl alcohol (water added with polyvinyl alcohol as a surfactant) is preferably used. Examples of the surfactant other than polyvinyl alcohol include lecithin, hydroxymethylcellulose, hydroxypropylcellulose and the like. When excess polyvinyl alcohol remains, a step for removing polyvinyl alcohol (removal step) by centrifugation and the like may be performed after a solvent evaporation step.

Examples of the good solvent include hardly water-soluble organic solvents having a low boiling point such as halogenated alkanes, acetone, methanol, ethanol, ethyl acetate, diethyl ether, cyclohexane, benzene, toluene and the like. For example, acetone causing less adverse influence on the environment and human body, and a mixture of acetone and methanol are preferably used.

The concentration of polyvinyl alcohol in an aqueous solution, the mixing ratio of acetone and methanol and the conditions of crystallization are not particularly limited and can be appropriately determined according to the kind of a drug to be contained in nanoparticles, particle size of spherically granulated crystals (nano order in the present invention) and the like. Adhesion of polyvinyl alcohol to the nanoparticle surface becomes more superior and redispersibility in water after drying becomes more improved as the concentration of polyvinyl alcohol in an aqueous solution increases; however, when the concentration of polyvinyl alcohol in the aqueous solution exceeds a given level, the viscosity of poor solvent increases and adversely affects the diffusibility of good solvent.

Although subject to change depending on the degree of polymerization and saponification value of polyvinyl alcohol, in the case the organic solvent is evaporated after nanoparticle formation and the nanoparticles are powderized by freeze-drying and the like, the concentration of polyvinyl alcohol in the aqueous solution is preferably not less than 0.1 wt % and not more than 10 wt %, more preferably about 2 wt %. In the case the organic solvent is evaporated from a suspension after nanoparticle formation and the nanoparticles are used for a step of carrying the nanoparticles on a stent, the concentration of polyvinyl alcohol in the aqueous solution is preferably set to not more than 0.5 wt %, particularly preferable about 0.1 wt %.

In addition, when nanoparticles are carried on a stent by the below-mentioned electrophoresis or spray method, a cationic polymer is preferably added to a poor solvent to positively charge the nanoparticle surface.

Examples of the cationic polymer include chitosan and chitosan derivatives; cationic cellulose wherein plural cationic groups are bonded to cellulose; polyamino compounds such as polyethyleneimine, polyvinylamine, polyallylamine and the like; polyamino acids such as polyornithine, polylysine and the like; polyvinylimidazole, poly(vinyl pyridinium chloride), alkylamino methacrylate quaternary salt polymer (DAM), alkylamino methacrylate quaternary salt-acrylamide copolymer (DAA) and the like, and chitosan or a derivative thereof is particularly preferably used.

Chitosan is a natural polymer wherein many glucosamine (one kind of sugar having an amino group) molecules are bound and is contained in the shells of prawn, crab and insects. Since chitosan characteristically has emulsion stability, shape retentive property, biodegradability, biocompatibility, antibacterial property and the like, it is widely used as a starting material of cosmetics, food, clothing materials, pharmaceutical products and the like. By the addition of chitosan to a poor solvent, highly safe nanoparticles free of an adverse influence on the living organisms can be produced.

Use of a chitosan derivative (cationic chitosan) such as N-[2-hydroxy-3-(trimethylammonio)propyl]chitosan chloride and the like having higher cationicity achieved by partially quaternarizing chitosan, which is cationic by nature, is preferable, since the repelling force between particles becomes strong and the stability of the particles is enhanced.

In addition, to improve the affinity and dispersion stability of a drug in a good solvent, a cationic lipid such as DOTAP and the like may be added to the good solvent to form a complex with the drug. However, the amount thereof to be added should be carefully determined because cationic lipid released in the cell may cause cytotoxicity.

The nanoparticles obtained as mentioned above can be processed into a redispersible aggregated particle composite (nanocomposite) during powderization by freeze-drying and the like. In this case, it is preferable to form a redispersible composite with an organic or inorganic substance, and dry the composite with the nanoparticles. When sugar alcohol or sucrose is applied, for example, sugar alcohol or sucrose becomes a excipient and the handling property of the nanoparticles can be enhanced. Examples of the sugar alcohol include mannitol, trehalose, sorbitol, erythritol, maltitose, xylitose and the like. Among these, trehalose is particularly preferable.

By forming a composite, a composite particle can be obtained which is an easily handlable aggregated particle of nanoparticles before use, and returns to nanoparticles upon contact with water when in use and restores the properties of high reactivity and the like. Alternatively, a fluidized bed drying granulation method (e.g., using Aglomaster AGM, manufactured by Hosokawa Micron Corporation) may be employed instead of the freeze-drying method to form a composite that enables integration in a redispersible state.

As a biocompatible polymer to be used in the present invention, a polymer which is mildly irritating and low toxic to living organisms, biocompatible, and biodegradable (disintegrated after administration and metabolized) is desirable. In addition, it is preferably a particle that gradually releases an encapsulated drug in a sustained manner. As such material, PLGA can be particularly preferably used.

The molecular weight (weight average molecular weight) of PLGA is preferably within the range of 5,000 to 200,000, more preferably 15,000 to 25,000. The composition ratio of lactic acid:glycolic acid is 1:99 to 99:1, and lactic acid:glycolic acid is preferably 1:0.333. Since PLGA having a content of lactic acid and glycolic acid within the range of 25 wt % to 65 wt % is amorphous and soluble in an organic solvent such as acetone and the like, it is preferably used.

Examples of the biodegradable, biocompatible polymer further include polyglycolic acid (PGA), polylactic acid (PLA), polyaspartic acid and the like. In addition, the copolymers thereof such as aspartic acid-lactic acid copolymer (PAL) and aspartic acid-lactic acid-glycolic acid copolymer (PALG) may also be used, and the polymer may also have a group that can be converted to an electrically charged group or functional group, such as amino acid.

Examples of the biocompatible polymer other than the above include polyalkylene such as polyethylene and polypropylene, polyvinyl compounds such as polyvinyl alcohol, polyvinyl ether and polyvinyl ester, polyamide, polycarbonate, polyethylene glycol, polyethylene oxide, poly(ethylene terephthalate), copolymer of acrylic acid and methacrylic acid, cellulose and other polysaccharides, and peptide or protein, and a copolymer thereof and a mixture thereof.

Thereafter, the obtained nanoparticle suspension is directly, or, where necessary, after evaporation of an organic solvent, which is a good solvent, under reduced pressure (solvent evaporation step) and further, where necessary, powderizing the nanoparticle by freeze-drying and the like, redispersed in water, and used for the next nanoparticle attachment step. Use of the nanoparticle in the form of a suspension directly for the next step is preferable, since the production step can be simplified due to the absence of freeze-drying and the like, and the amount of polyvinyl alcohol to be added to a poor solvent can be reduced.

When nanoparticles are to be powderized, it is preferable to convert them to a redispersible aggregated particle composite together with a binder (for example, trehalose etc.) to give a composite particle, since an easily handlable aggregated particle of nanoparticles before use can be obtained, which returns to nanoparticles upon contact with water when in use, which dissolves the binder.

When nanoparticles are to be carried on a stent by the below-mentioned electrophoresis or spray method, the obtained nanoparticles are preferably mixed with a solution of a cationic polymer to positively charge the nanoparticle surface. As the cationic polymer, those similar to the above examples can be mentioned. Particularly, chitosan or a derivative thereof is preferably used. As a solvent to be used for the cationic polymer solution, those exemplified as the aforementioned "poor solvent" can be mentioned. Particularly, an aqueous solution of a cationic polymer is preferably used. The concentration of the cationic polymer in the solution is preferably not less than 0.01 wt % and not more than 1.0 wt %.

The drug-containing nanoparticle to be used in the present invention is not particularly limited as long as it has an average particle size of less than 1,000 nm. To enhance the delivery efficiency to an affected part, an average particle size is preferably set to not more than 600 nm, more preferably not more than 500 nm, and still more preferably 100 nm to 400 nm and the like.

In the present invention, the average particle size of nanoparticles means an average particle size measured by a dynamic light scattering method.

The salt of pioglitazone is not particularly limited as long as it is a pharmaceutically acceptable salt, and examples of the salt include salts with inorganic acids (e.g., salts with hydrochloric acid, hydrobromic acid, nitric acid, sulfuric acid, phosphoric acid etc.); salts with organic acids (e.g., salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid etc.), and the like. Preferred is hydrochloride.

The content of pioglitazone or a salt thereof in nanoparticles can be controlled by adjusting the amount of a drug to be added during nanoparticle formation, the kind and the amount of a cationic polymer to be added, and the kind of the biocompatible polymer that forms nanoparticles. The content of pioglitazone or a salt thereof in nanoparticles is preferably 0.1 to 10 wt %, more preferably 1 to 10 wt %, as pioglitazone.

Since a drug (pioglitazone or a salt thereof) can be safely and efficiently delivered to a target site (blood vessel) by carrying the nanoparticles of the present invention on a stent, the method can be an effective method for the prophylaxis or treatment of arteriosclerotic diseases and the like.

As a method of carrying nanoparticles on a stent, a method comprising physically attaching nanoparticles to a stent body by immersion in a nanoparticle suspension, mist coating and the like can be used. Alternatively, a method comprising adding a cationic polymer compound to nanoparticles to positively charge the nanoparticle surface, and electrically attaching the nanoparticles to coat the stent body firmly and uniformly can also be used. Examples of such method include (1) electrophoresis comprising electrification in a biocompatible nanoparticle suspension with a stent body as a negative electrode, and (2) a spray method comprising attaching biocompatible nanoparticle-containing droplets onto a negatively charged stent surface. These methods can be performed according to the method described in JP-A-2007-215620.

The shape of the stent body may be formed by knitting and molding a fiber material, cutting a metal pipe into a net structure by laser and the like, or conventionally-known various shapes such as a crown shape, a cylindrical shape and the like can be used. The stent body may be of a balloon expansion type or a self-expansion type, and the size of the stent body can be appropriately determined according to the site of application. For example, when used for the heart coronary artery, the outer diameter before expansion is generally preferably 1.0 to 3.0 mm and the length is about 5.0 to 50 mm.

When nanoparticles are attached by electrophoresis, moreover, the stent body needs to be made of a conductive material such as a metal and the like. Examples of the metal used for the stent body include stainless, magnesium, tantalum, titanium, nickel-titanium alloy, Inconel (registered trademark), gold, platinum, iridium, tungsten, cobalt alloy and the like. When the stent is of a self-expansion type, superelastic alloys such as nickel-titanium etc., and the like are preferable, since restoration of the original shape is required. On the other hand, when it is of a balloon expansion type, stainless and the like, which do not easily restore the original shape after expansion, are preferable, and SUS316L most superior in the corrosion resistance is preferably used.

Examples of the conductive material other than metals include conductive polymers such as polyaniline, polypyrrole, polythiophene, polyisothianaphtene, polyethylenedioxythiophene and the like, conductive ceramic and the like. Alternatively, a non-conductive resin imparted with conductivity by adding a conductive filler, or by a conductive treatment of the surface by coating and the like may be used.

When a non-biodegradable material such as stainless and the like is used as a material of the stent body, since an inflammation may be developed on the blood vessel inner wall due to long-term stenting, thus possibly causing restenosis, percutaneous transluminal coronary angioplasty (PTCA) needs to be performed every several months for re-stenting, which places a heavy burden on patients. However, since a stent body made of magnesium, a biodegradable metal, is gradually degraded in the body and disappears in several months after stenting, the development of inflammation due to stenting can be suppressed.

Particularly, by attaching nanoparticles formed of a biodegradable polymer such as PGA, PLA, PLGA, PAL and the like as a biocompatible polymer to a magnesium stent body, a drug eluting stent (DES) which completely disappears in a given period after stenting in the body and less burdensome on living organisms can be provided. In this case, the biodegradable polymer used for forming the nanoparticles preferably has a lower biodegradation rate than that of a biodegradable polymer to penetrate into a nanoparticle layer in the below-mentioned immersion step.

Here, since the amount of nanoparticles attracted to the stent surface per unit hour during electrophoresis increases as a higher voltage is applied between the positive electrode and the negative electrode, a nanoparticle layer can be formed on the stent surface in a short time. On the other hand, since a large amount of nanoparticles attaches, a uniform nanoparticle layer is difficult to form. Thus, the voltage to be applied during electrophoresis can be appropriately set according to the desired uniformity and formation efficiency of the nanoparticle layer.

The spray method is now explained. The spray method comprises electrically attaching fine suspension droplets of positively charged biocompatible nanoparticles to the surface of a negatively charged stent body by electrification.

Examples thereof include an ultrasonic misting method comprising misting a nanoparticle suspension by ultrasonication, a spray method or an airbrush method comprising blowing a nanoparticle suspension against a stent surface using a spraying apparatus or airbrush, and the like.

In the spray method, the stent body is also negatively charged by electrification. Therefore, as in the case of electrophoresis, a positively charged-modified nanoparticle layer attaches markedly firmly as compared to a spray treatment without electrification of the stent body, and a DES showing good adhesion between the stent body and nanoparticles and superior in the corrosion resistance can be produced. In addition, since nanoparticles in the droplets actively attach to the stent body, the attachment efficiency of nanoparticles to the side and backside of a stent, where misted or sprayed droplets are difficult to attach directly, can also be increased. The explanation of the shape and material of the stent body to be subjected to the spray method is omitted, since it is the same as in the case of electrophoresis.

In addition to the step of forming a nanoparticle layer on the stent surface by electrophoresis or spray method, moreover, a step of laminating a nanoparticle layer thereon (hereinafter to be referred to as second attachment step) can also be set. In the second attachment step, since a new nanoparticle layer is laminated along the uniform nanoparticle layer formed on the stent surface, even if the amount of the nanoparticles attached per unit hour is increased, a nanoparticle layer having a desired layer thickness can be uniformly and efficiently formed. The aforementioned electrophoresis, ultrasonic misting method, spray method, airbrush method and the like can be used for the second attachment step. When the ultrasonic misting method, spray method, airbrush method and the like are used for the second attachment step, a stent body is preferably negatively charged to more efficiently and firmly laminate the nanoparticle layer.

Without any treatment, the nanoparticle layer formed on the stent surface is dissolved at once in a short time after setting in the body, and control of sustainability of the drug efficacy becomes difficult. On the other hand, when the nanoparticle layer is completely dried, nanoparticles are more firmly aggregated with each other to form an insoluble nanoparticle coating layer, which may prevent dissolution of the nanoparticles from the stent surface and incorporation into the cells. As mentioned above, therefore, it is preferable to form a nanoparticle layer on a stent surface, immerse the nanoparticle layer in a solution of a biodegradable polymer before the layer is completely dried (immersion step), and solidify the layer by drying (drying step).

When the nanoparticle layer formed on the stent surface and before complete drying is immersed in a solution of a biodegradable polymer, the biodegradable polymer solution penetrates into the clearance between nanoparticles forming the nanoparticle layer. When the solvent used for dissolution of the biodegradable polymer and water remaining in the nanoparticle layer are dried, a biodegradable polymer layer is formed. As a result, each nanoparticle is retained free of aggregation due to the biodegradable polymer, and the nanoparticles are gradually eluted out due to the degradation of the biodegradable polymer layer after setting the DES in the body.

Examples of the biodegradable polymer include microorganism-derived polymers such as polyhydroxybutyrate, polyhydroxyvalerate and the like, collagen, cellulose acetate, bacterial cellulose, high-amylose corn starch, starch, natural polymers such as chitosan etc., and the like. Of these, collagen and the like having a faster degradation rate in the body than the biocompatible polymers used for the formation of nanoparticles such as PLGA and the like are more preferably used. By appropriately selecting the kind, molecular weight and the like of such biodegradable polymer, the elution rate of nanoparticles attached to the stent surface becomes controllable. While PGA, PLA, PLGA, PAL and the like can also be used as biodegradable polymers, one having a smaller molecular weight is used to exceed the degradation rate of the nanoparticles.

In the DES obtained as the above, since nanoparticles carried on the stent body have positively charged surface, cell adhesion thereof after elution from the stent surface increases. As a result, the introduction efficiency of nanoparticles to the cells in the lesion site where the stent is placed can be increased.

By addition of a drug (pioglitazone or a salt thereof) to a biodegradable polymer solution in which the nanoparticle layer is immersed, moreover, the drug contained in the biodegradable polymer layer in the outer part of the nanoparticles can be fast acting, and the drug contained inside the nanoparticles can be slow and continuously acting. The drug content of the nanoparticles and stent can be appropriately determined according to the required immediate effect, level of sustainability and the like.

Namely, when long-term sustainability of the effect after administration is required, the drug only needs to be contained inside the nanoparticles, and when expression of the effect from immediately after administration is required, the drug only needs to be also contained in the biodegradable polymer layer in the outer part of the nanoparticles.

The content of pioglitazone or a salt thereof in the stent of the present invention is preferably 1 to 1000 more preferably 10 to 50 μg, as pioglitazone.

The drug-containing nanoparticles of the present invention can be safely administered alone or in the form of a pharmaceutical preparation (pharmaceutical composition) containing a pharmacologically acceptable carrier according to a conventional method, for example, tablet (including sugar-coated tablet, film-coated tablet and the like), powder, granule, capsule, liquid, emulsion, suspension, injection, inhalant, suppository, sustained-release preparation (e.g., sublingual tablet, microcapsule etc.), plaster, orally disintegrating tablet, orally disintegrable films and the like, orally or parenterally (e.g., subcutaneous, topical, rectal, intravenous, intraarterial, intratracheal, transpulmonary administrations etc.). The pharmaceutical preparation of the present invention is preferably administered parenterally, more preferably by intravenous administration, intraarterial administration, intratracheal administration, transpulmonary administration and the like.

Examples of the above-mentioned pharmacologically acceptable carrier include various organic and inorganic carrier substances conventionally used as preparation materials, such as excipient, lubricant, binder and disintegrant for solid preparations, solvent, solubilizing agent, suspending agent, isotonicity agent, buffer agent and soothing agent for liquid preparation, and the like. Where necessary, a generally used additive such as preservative, antioxidant, colorant, sweetening agent, adsorbent, wetting agent and the like can also be used as appropriate in a suitable amount.

Examples of the excipient include lactose, sucrose, D-mannitol, starch, cornstarch, crystalline cellulose, light anhydrous silicic acid and the like. Examples of the lubricant include magnesium stearate, calcium stearate, talc, colloidal silica and the like. Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like. Examples of the disintegrant include starch, carboxymethylcellulose, calcium carboxymethylcellulose, croscarmellose sodium, sodium carboxymethyl starch, low-substituted hydroxypropylcellulose and the like. Examples of the solvent include water for injection, alcohol, propylene glycol, macrogol, sesame oil, corn oil, olive oil and the like. Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like. Examples of the isotonicity agent include glucose, D-sorbitol, sodium chloride, glycerol, D-mannitol and the like. Examples of the buffer agent include buffers such as phosphate, acetate, carbonate, citrate etc. and the like. Examples of the soothing agent include benzyl alcohol and the like. Examples of the preservative include paraoxybenzoates, chlorobutanol, benzyl alcohol, phenethyl alcohol, dehydroacetic acid, sorbic acid and the like. Examples of the antioxidant include sulfite, ascorbic acid, α-tocopherol and the like.

The dose of pioglitazone or a salt thereof varies depending on the subject of administration, administration route and symptom, and is not particularly limited. For example, for intraarterial administration to an adult patient for the treatment of arteriosclerotic diseases, the dose of the active ingredient pioglitazone is about 1 to about 560 mg, preferably about 1 to about 200 mg, more preferably about 1 to about 100 mg, which is desirably administered in about 1 to 3 portions a day depending on the symptom.

The content of pioglitazone or a salt thereof in the pharmaceutical preparation (pharmaceutical composition) of the present invention is about 0.1 to about 10 wt % of the whole preparation (composition).

The nanoparticles of the present invention has a superior plaque rupture development suppressive action, plaque stabilizing action, monocyte chemotactic factor (MCP-1) production suppressive action, stable long-term retention action at vascular lesion site, neointimal formation suppressive action after vascular injury, angiogenesis promotive action in ischemic site and the like.

The nanoparticles, pharmaceutical preparation and stent of the present invention are low toxic and can be used for the prophylaxis or treatment of, for example, arteriosclerotic diseases. Examples of the arteriosclerotic diseases include arteriosclerosis (e.g., atherosclerosis etc.), myocardial infarction, (acute) coronary syndrome such as unstable angina pectoris and the like, peripheral arterial occlusion, restenosis after percutaneous transluminal coronary angioplasty (PTCA), restenosis after stenting, ischemic cardiac diseases (e.g., angina pectoris etc.), intermittent claudication, cerebral apoplexy, cerebral infarction, cerebral embolism, cerebral hemorrhage, lacunar infarction, cerebrovascular dementia, hypercholesterolemia, hypertriglyceridemia, hypoHDL-emia, hyperlipidemia and the like.

In addition, the nanoparticles, pharmaceutical preparation and stent of the present invention can also be used for the prophylaxis or treatment of in-stent restenosis.

Furthermore, the nanoparticles, pharmaceutical preparation and stent of the present invention can be used for the prophylaxis or treatment of diseases involving MCP-1 (e.g., inflammatory disease etc.). Examples of the inflammatory diseases include lung disease such as lung fibrosis, chronic obstructive pulmonary disease (COPD), pulmonary hypertension etc. and the like.

EXAMPLES

The present invention is explained in more detail in the following by referring to Examples and Experimental Examples, which are not to be construed as limitative.

Example 1

Preparation of Pioglitazone-Containing PLGA Nanoparticles

An aqueous solution of 0.5 wt % polyvinyl alcohol (Gosenol EG-05 (registered trademark), manufactured by The Nippon Synthetic Chemical Industry Co., Ltd.) was prepared and used as a poor solvent. In addition, lactic acid-glycolic acid copolymer (PLGA7520, lactic acid/glycolic acid=75/25, weight average molecular weight 20,000, Wako Pure Chemical Industries, Ltd.) (1 g) was dissolved in acetone (40 mL) and mixed with pioglitazone hydrochloride (40 mg) in methanol (20 mL), and the mixture was used as a polymer solution. The solution was added dropwise at 4 mL/min to the earlier-obtained poor solvent at 40° C. with stirring at 400 rpm to give a pioglitazone-containing PLGA nanoparticle suspension. Acetone and methanol were evaporated under reduced pressure for 1.5 hr, and the residue was freeze-dried to give a pioglitazone-containing PLGA nanoparticle powder.

The redispersibility of the obtained powder in water was good. The average particle size of the nanoparticle powder after redispersion in purified water was measured by a dynamic light scattering method and found to be 314 nm. The content of pioglitazone in the nanoparticle powder was 2.37 wt %.

Experimental Example 1

Plaque Rupture Suppressive Effect in ApoE-Knockout Mouse

Using the pioglitazone-containing nanoparticles obtained in Example 1, a plaque rupture suppressive effect was tested in ApoE-knockout mouse.
(1) Experimental Animal Male ApoE-knockout mouse (C57Bl/6J background) was purchased from Jackson Laboratory (USA) and used. The mouse was allowed water drinking and bred on a normal diet until the start of the test.
(2) Diet and Angiotensin II Administration A high fat diet (containing 21% lard and 0.15% cholesterol) was given to a ApoE-knockout mouse from 16 weeks of age, and intraperitoneal administration of angiotensin II (1.9 mg/kg/day) was started from 20 weeks of age.
(3) Administration Method and Dose PLGA nanoparticles (8.75 mg/mouse/week) free of a drug was administered to the control group.

The pioglitazone-containing PLGA nanoparticles obtained in Example 1 was administered (8.75 mg/mouse/week, containing 210 μg as pioglitazone, corresponding to 7 mg/kg/week) to the pioglitazone-containing nanoparticle group.

Respective nanoparticles (8.75 mg) were suspended in phosphate buffered saline (0.5 mL), and intravenously administered from 20 to 23 weeks of age once a week, 4 times total.

(4) Evaluation Method

After administration of angiotensin II for 28 days, the right brachiocephalic artery was washed and fixed with phosphate buffered saline and neutral buffered formalin via the heart, and isolated. A paraffin section was prepared, stained with Elastica van Gieson, and the plaque rupture and thickness of fibrous cap were evaluated.

(5) Results

The results are shown in Table 1.

TABLE 1

|  | Control group | Pioglitazone-containing nanoparticle group |
|---|---|---|
| Acute plaque rupture | 7/11 (64%) | 1/8 (13%)* |
| Total plaque rupture (/mouse) | 3.1 ± 0.4 | 1.1 ± 0.4* |
| Buried fibrous caps (/mouse) | 2.8 ± 0.4 | 0.9 ± 0.3* |
| Fibrous cap thickness (μm) | 1.6 ± 0.3 | 3.6 ± 0.8* |

*$P < 0.05$ vs control group

Therefrom it was found that administration of pioglitazone-containing nanoparticles significantly suppresses the development of plaque rupture in an arteriosclerosis model, ApoE-knockout mouse. In addition, it was also found that administration of pioglitazone-containing nanoparticles significantly increases the thickness of fibrous cap, and stabilizes the plaque.

Experimental Example 2

Suppressive Effect on Monocyte Chemotactic Factor (MCP-1) Production by THP-1

(1) Experimental Method

Human monocyte cell line, THP-1 (obtained from Health Science Research Resources Bank, Japan Health Sciences Foundation) was adjusted to $5 \times 10^5$ cells/well/500 μL with RPMI medium containing 0.5% fetal bovine serum and 1% penicillin, and plated on a 48-well plate (day 0). On day 1, pioglitazone hydrochloride, or the pioglitazone-containing PLGA nanoparticles obtained in Example 1 (concentration as pioglitazone; 1.0, 10 μM) was added, and stimulated on day 2 by addition of LPS 1 μg/mL.

(2) Evaluation Method

On day 3, the supernatant was collected, and MCP-1 was assayed using a human MCP-1 ELISA kit (BIOSOURCE).

(3) Results

It was found that, using pioglitazone-containing nanoparticles, an MCP-1 production suppressive effect can be achieved by the administration of a smaller amount of pioglitazone.

Experimental Example 3

By a method similar to that in Example 1, fluorescein isothiocyanate (FITC)-containing nanoparticles (fluorescence dye) were prepared, and in vivo kinetics after intravenous injection to an ApoE-knockout mouse was tested.

(1) FITC-Containing Nanoparticles

By a treatment in, the same manner as in Example 1 except that FITC (100 mg) was used instead of pioglitazone hydrochloride, a FITC-containing nanoparticle powder was obtained.

(2) Experimental Animal

Male ApoE-knockout mouse (C57Bl/6J background) was purchased from Jackson Laboratory (USA) and used. The mouse was allowed water drinking and bred on a normal diet until the start of the test.

(3) Diet and Angiotensin II Administration

A high fat diet (containing 21% lard and 0.15% cholesterol) was given to an ApoE-knockout mouse from 16 weeks of age, and intraperitoneal administration of angiotensin II (1.9 mg/kg/day) was started from 20 weeks of age.

(4) Administration Method, Dose and Evaluation Method

The FITC-containing nanoparticles (8.75 mg) obtained in (1) were suspended in phosphate buffered saline (0.5 mL), and intravenously administered to the mouse (21-week-old). After 2 hr, the venous blood was collected, and leukocyte after hemolysis of red blood cell was stained with anti-CD11b or anti-Gr-1 antibody labeled with TexasRed and examined by flow cytometry. Also, 48 hr later, the right brachiocephalic artery was isolated, a paraffin section was prepared, and macrophage showing FITC uptake in arteriosclerotic plaque was identified by HE stain and FITC immunostaining.

(5) Results

When FITC-containing nanoparticles were intravenously injected to the mouse, selective FITC uptake was observed in CD11b(+)Gr-1(−) monocytes in the peripheral blood 2 hr later. When the right brachiocephalic artery was isolated 48 hr later and histologically examined, FITC immunostaining was observed in macrophages in the brachiocephalic artery and arteriosclerotic lesions.

Therefrom it was found that the nanoparticle of the present invention can be a monocyte/macrophage selective carrier.

Experimental Example 4

Control of Macrophage Gene Expression by Pioglitazone-Containing Nanoparticles

The effect on macrophage gene expression by intravenous injection of pioglitazone-containing nanoparticles obtained in Example 1 was tested.

(1) Experimental Animal

Male ApoE-knockout mouse (C57Bl/6J background) was purchased from Jackson Laboratory (USA) and used. The mouse was allowed water drinking and bred on a normal diet until the start of the test.

(2) Diet and Angiotensin II Administration

A high fat diet (containing 21% lard and 0.15% cholesterol) was given to an ApoE-knockout mouse from 16 weeks of age, and intraperitoneal administration of angiotensin II (1.9 mg/kg/day) was started from 20 weeks of age.

(3) Administration Method and Dose

PLGA nanoparticles (8.75 mg/mouse/week) free of a drug were administered to the control group.

The pioglitazone-containing PLGA nanoparticles obtained in Example 1 (8.75 mg/mouse, containing 210 μg as pioglitazone, corresponding to 7 mg/kg body weight) were administered to the pioglitazone-containing nanoparticle group.

Respective nanoparticles (8.75 mg) were suspended in phosphate buffered saline (0.5 mL) and administered once at 21 weeks of age by intravenous injection.

(4) Evaluation Method

Simultaneously with the intravenous injection of PLGA nanoparticles or pioglitazone-containing nanoparticles, thioglycolate medium (Difco, 2 mL) was administered intraperitoneally. After 3 days, intraperitoneal macrophage to was collected, and mRNA was extracted. Various gene expressions in the macrophages of the control group and pioglitazone-containing nanoparticle group were measured by RT-PCR, and the expression levels were compared.

(5) Results

The genes that showed remarkably increased or suppressed expression in the pioglitazone-containing nanoparticle group macrophage as compared to the control group macrophage are shown in Table 2. In the pioglitazone-containing nanoparticle group macrophages, the expression of ABCA1, that promotes reverse cholesterol transport, was increased, whereas the expression of CC chemokines such as MCP-1, RANTES and the like, which are monocyte chemotactic factors, was suppressed.

TABLE 2

| Gene with promoted expression | Fold | Gene with suppressed expression | Fold |
| --- | --- | --- | --- |
| ATP-binding cassette A1 (ABCA1) | 1.91 | CCL2/MCP-1 CL5/RANTES | 0.44 0.21 |

Therefrom it was found that the pioglitazone-containing nanoparticles administered were selectively delivered to monocyte/macrophage in the body of the ApoE-knockout mouse and could control gene expression including MCP-1 suppression.

Experimental Example 5

Neointimal Formation Suppressive Effect in Mouse Vascular Injury Model

Using the pioglitazone-containing nanoparticles obtained in Example 1, the neointimal formation suppressive effect in mouse vascular injury model was tested.

(1) Experimental Animal

Male wild-type mouse (C57Bl/6J) was purchased from CLEA Japan, Inc. and used. The mouse was allowed water drinking and food consumption, and bred on a normal diet until the start of the test.

(2) Preparation of Vascular Injury Model

An 8- to 10-week-old wild-type mouse was deeply anesthetized with pentobarbital, and the right femoral artery was exposed. The both ends of the blood vessel were ligated with a 6-0 silk thread to temporarily shut off the blood flow. The branch was incised, and a wire (diameter 0.15 inch, No. C—SF-15-15, COOK) was inserted by 5 mm in the iliac artery side to injure the blood vessel.

(3) Administration Method and Dose

After wire injury, the experimental animals were divided into a solvent control group and pioglitazone-containing nanoparticle group. The wire was removed, 100 μl, each of a solvent and a pioglitazone-containing PLGA nanoparticle solution was intraarterially administered from the branch over 5 min.

The solvent control group was administered with the solvent (phosphate buffered saline) alone only once.

The pioglitazone-containing nanoparticle group was administered with the pioglitazone-containing PLGA nanoparticles obtained in Example 1 (containing 0.5 mg/mouse as nanoparticles, corresponding to pioglitazone concentration of 0.015 mg/mouse (0.5 mg/kg body weight)) once. After administration, the branch part was ligated, the blood flow was resumed and the skin was sutured.

Immediately after the wire injury, a high dose (10-fold amount of clinical dose) pioglitazone hydrochloride (0.15 mg/mouse (5 mg/kg body weight) as pioglitazone) single time intraperitoneal administration group was formed.

(4) Evaluation Method

At 28 days after vascular injury, the right femoral artery was washed and fixed with phosphate buffered saline and neutral buffered formalin via the heart, and isolated. A paraffin section was prepared and stained with Elastica van Gieson, proliferating cell nuclear antigen (PCNA) was immunohistochemically stained, and evaluated for the intima/media ratio, neointimal area, medial area and cell proliferation. For immunohistochemical staining, the proliferated cells were counted and the ratio of thereof to the total cell number was calculated.

(5) Results

The results are shown in Table 3 and Table 4. The administration of pioglitazone-containing nanoparticles resulted in a remarkable decrease in the intima/media ratio and neointimal area as compared with the solvent control group. In addition, the pioglitazone-containing nanoparticles more strongly suppressed proliferation of smooth muscle cells than pioglitazone hydrochloride. Since neointimal formation progresses due to migration of smooth muscle cell from the media to the intima and proliferation, the contribution of the proliferation suppressive action to the suppression of neointimal formation by pioglitazone-containing nanoparticles was shown.

TABLE 3

| Index | Solvent control group | Pioglitazone-containing nanoparticle group |
| --- | --- | --- |
| Intima/media ratio | 3.2 ± 0.7 | 1.3 ± 0.3* |
| Neointimal area ($\mu m^2$) | 31816 ± 8526 | 14871 ± 2677* |
| Medial area ($\mu m^2$) | 15835 ± 1065 | 17160 ± 1205 |
| Proliferated cell rate | 0.57 ± 0.02 | 0.25 ± 0.08* |

*P < 0.05 vs control group

TABLE 4

| Index | Pioglitazone high dose systemic administration group | Pioglitazone-containing nanoparticle group |
| --- | --- | --- |
| Intima/media ratio | 2.3 ± 1.2 | 1.3 ± 0.3* |
| Neointimal area ($\mu m^2$) | 23656 ± 8982 | 14871 ± 2677* |
| Medial area ($\mu m^2$) | 14904 ± 2107 | 17160 ± 1205 |

*P < 0.05 vs high dose systemic administration group

Therefrom it was found that administration of pioglitazone-containing nanoparticles significantly suppresses neointimal formation in the blood vessels after vascular injury. In addition, it was clarified that the pioglitazone-containing nanoparticles have a stronger action than a 10-fold amount of pioglitazone hydrochloride. The action mechanism thereof was clarified to partially involve a smooth muscle cell overproliferation suppressive action.

Experimental Example 6

Quick Delivery of Nanoparticles to Cultured Rat Coronary Artery Smooth Muscle Cell and Long-Term Retention Effect Thereof Using the FITC-containing nanoparticles prepared in Experimental Example 3 (1), deliver and retention tests in cultured rat coronary artery smooth muscle cell were performed.

(1) Experimental Method

Rat aortic smooth muscle cells (obtained from TOYOBO) were plated on a slide glass chamber to a subconfluent cell density in DMEM medium (Sigma) containing 10% fetal bovine serum (day 0). On day 2, the medium was changed to a medium containing FITC or FITC-containing nanoparticles (0.5 mg/mL in nanoparticles concentration).

(2) Evaluation Method

At 5 min and 24 hr after medium exchange, the cells were fixed with methanol, the nucleus was stained with Propidium iodide (Vector laboratories, Inc.), and subjected to fluorescence microscope observation. The total number of nuclei and fluorescence positive cells were counted for each field of view, and the ratio of fluorescence positive cells was calculated.

(3) Results

The cells added with a medium containing FITC alone did not show positive cell at all (0%), but the cells added with a medium containing FITC-containing nanoparticles showed 90% or more of fluorescence positive cells in 5 min, and 90% or more of fluorescence positive cells even after 24 hr. That is, it was clarified that FITC-containing nanoparticles were delivered to cultured rat aortic smooth muscle cells at a high rate in an extremely short period of 5 min, and stably retained for a long term of 24 hr and longer. Accordingly, it is suggested that the pioglitazone-containing nanoparticles prepared in Example 1 has an effect of a similar quick delivery to the coronary artery smooth muscle cells and retention for a long time.

Experimental Example 7

Suppressive Effect on Proliferation of Cultured Human Coronary Artery Smooth Muscle Cell Using the pioglitazone-containing nanoparticles obtained in Example 1, a growth suppressive effect on cultured human coronary artery smooth muscle cells was tested.

(1) Experimental Method

Human coronary artery smooth muscle cells (purchased from Lonza Walkersville Inc., Walkersville, Md., USA) were adjusted to $5 \times 10^3$ cells/well/500 µL with SmBM medium (Lonza) containing 5% fetal bovine serum and 1% penicillin, and plated on a 48-well plate (day 0). On day 2, the medium was changed, and starvation state was produced with an SmBM medium containing 0.1% fetal bovine serum and 1% penicillin for 2 days. On day 3, the solvent (phosphate buffered saline) alone or the pioglitazone-containing PLGA nanoparticles obtained in Example 1 (concentration as pioglitazone; 10 µM) was/were added, and the cells were cultured in an SmBM medium containing 10% fetal bovine serum and 1% penicillin for 3 days. The human coronary artery smooth muscle cell proliferation activity of 10% fetal bovine serum is widely known, and this was used as a growth stimulating agent in this test.

(2) Evaluation Method

At day 7 from the start of the culture, the cells were fixed with methanol, stained with Diff-Quick staining solution (purchased from Sysmex Corporation) and the cell number per field of view was counted.

(3) Results

The results are shown in Table 5. In the pioglitazone-containing nanoparticle group, the smooth muscle cell proliferation by 10% fetal bovine serum stimulation was remarkably suppressed.

TABLE 5

| Index | Solvent control group, stimulation alone | Pioglitazone-containing nanoparticle group |
|---|---|---|
| Cell number/field of view | 64.4 ± 5.9 | 34.4 ± 2.6* |

*$P < 0.05$ vs control group

Therefrom it was clarified that the pioglitazone-containing nanoparticles prepared in Example 1 had a strong vascular smooth muscle cell proliferation suppressive action.

Example 2

(1) Preparation of Pioglitazone-Containing Chitosan-Modified PLGA Nanoparticles PLGA (PLGA7520, lactic acid/glycolic acid=75/25, weight average molecular weight 20,000, manufactured by Wako Pure Chemical Industries, Ltd.) (2 g) was dissolved in acetone (20 mL), and pioglitazone hydrochloride (100 mg) dissolved in methanol (10 mL) was added to give a polymer solution. The solution was added dropwise at a constant rate of 4 mL/min to an aqueous solution (50 mL) of 2 wt % polyvinyl alcohol (PVA, manufactured by KURARAY CO., LTD.) with stirring at 40° C. At this time, an emulsion droplet of a nanometer size is prepared due to a self-emulsion action caused by the turbulence in the emulsion droplet surface by mutual diffusion of acetone, methanol and water. Thereafter, acetone and methanol were evaporated and the obtained PLGA nanoparticle suspension was centrifuged (centrifuge acceleration 41000 G, −20° C., 20 min) to give PLGA nanoparticle precipitate, which was resuspended in purified water to remove excess PVA not adsorbed on the PLGA surface. Thereto was added an aqueous solution (50 mL) of 0.02 wt % chitosan (manufactured by Katakura Chikkarin Co., Ltd.), and the mixture was stirred for 1 hr and freeze-dried at −45° C. to powderize pioglitazone-containing chitosan-modified PLGA nanoparticles.

The redispersibility of the obtained powder in water was good. The average particle size of the nanoparticle powder after redispersion in purified water was measured by a dynamic light scattering method and found to be 584 nm. The content of pioglitazone in the nanoparticle powder was 2.42 wt %.

(2) Production of Pioglitazone-Containing Nanoparticle Eluting Stent

The pioglitazone-containing chitosan-modified PLGA nanoparticles obtained in (1) were suspended in purified water to give a nanoparticle (0.25 wt %) suspension. A stainless (SUS316L) multi-link stent (length 15 mm) was passed through a stainless pipe (inner diameter 1.1 mm, outer diameter 1.3 mm) before stent processing to give a negative electrode. A carbon rod was set as a positive electrode. The nanoparticle suspension was filled in an electrolytic bath (inner diameter 8.5 mm, outer diameter 9.5 mm, height 23 mm) with an upper open surface, and the stainless pipe mounted with a stent body was stood upright in the electrolytic bath so that the stent body would be completely immersed in the nanoparticle suspension and a part of the stainless pipe would protrude from the liquid surface. Then, an external power supply apparatus (DC power supply, Nippon Stabilizer Industry Co., Ltd.) and an ampere meter were serially connected so that the carbon rod would be a positive electrode and the stainless pipe would be a negative electrode, and the voltage was adjusted to maintain an electric current 5 mA constant voltage, and electricity was applied for 10 min. Since the stent body and the stainless pipe were produced from the same material and had the same conductivity, the stent body could be uniformly electrified. After the completion of the electrification, the stent body was removed from the stainless pipe and dried.

Experimental Example 8

Restenosis Suppressive Effect in Primate in-Stent Stenosis Model

Using the pioglitazone-containing nanoparticle eluting stent obtained in Example 2, the restenosis suppressive effect in a primate in-stent stenosis model was tested.
(1) Experimental Animal Male 5-year old cynomolgus monkey (*Macaca fascicularis*) was purchased from Primate Corporation and used. The monkey was allowed water drinking, and bred on a normal diet until the start of the test.
(2) Diet A high fat diet (containing 0.5% cholesterol) was given from the start of the test to the anatomy.
(3) Evaluation Method At 1 month from the start of the test, the pioglitazone-containing nanoparticle eluting stent obtained in Example 2, an FITC-containing nanoparticle eluting stent and a bare metal stent were placed in the left and right iliac arteries. At 28 days from the stenting, the artery where the stent had been set was washed and fixed with phosphate buffered saline and neutral buffered formalin via the heart, and isolated. A resin section was prepared, stained with hematoxylin-eosin, and the neointimal area was evaluated.
(4) Results The results are shown in Table 6.

TABLE 6

|  | Bare metal stent group | FITC-containing nanoparticle eluting stent group | Pioglitazone-containing nanoparticle eluting stent group |
| --- | --- | --- | --- |
| Neointimal area (mm$^2$) | 2.6 ± 0.3 | 2.3 ± 0.2 | 1.7 ± 0.1*† |

*P < 0.05 vs bare metal stent group,
†P < 0.05 vs FITC-containing nanoparticle eluting stent group Therefrom it was found that a pioglitazone-containing nanoparticle eluting stent significantly suppresses the neointimal formation after stenting and suppresses restenosis.

Experimental Example 9

Angiogenesis Promoting Effect of Pioglitazone-Containing Nanoparticles in Mouse Hind Limb Ischemia Model Using the pioglitazone-containing nanoparticles obtained in Example 1, the angiogenesis promoting effect in mouse hind limb ischemia model was tested.
(1) Experimental Animal Male wild-type mouse (C57BL/6J) was purchased from CLEA Japan, Inc. and used. The mouse was allowed water drinking and food consumption, and bred on a normal diet until the end of the test.
(2) Preparation of Hind Limb Ischemia Model An 8-week-old wild-type mouse was deeply anesthetized with pentobarbital, and the left femoral artery/vein was exposed. The superficial femoral artery and vein (from under deep femoral artery and vein to popliteal artery and vein) were ligated with a 6-0 silk thread and incised to give an ischemia model.
(3) Administration Method and Dose After preparation of the hind limb ischemia model, the experimental animals were divided into 2 groups of (1) solvent control group, and (2) pioglitazone-containing nanoparticle group. Immediately after preparation of the model, a solvent or a suspension obtained by suspending pioglitazone-containing nanoparticles in a solvent (0.9 mg/100 μL as nanoparticles, 0.027 mg/100 μL as pioglitazone concentration) were each intramuscularly injected by 100 μL into the left thigh muscle (corresponding to dose 1.125 mg/kg). As the solvent, phosphate buffered saline was used. After the administration, the skin was sutured.
(4) Evaluation Method At day 21 after ischemia, the blood flow of the ischemic limb (left limb) and non-ischemic limb (right limb) was evaluated using a laser Doppler perfusion image (LDPI) analyzer (Moor Instruments). The hind limb blood flow ratio was determined as a ratio of the LDPI signal of the ischemic limb to that of the non-ischemic limb.
(5) Results The results are shown in Table 7.

TABLE 7

|  | Solvent control group | Pioglitazone-containing nanoparticle group |
| --- | --- | --- |
| hind limb blood flow ratio (ischemic limb/non-ischemic limb) | 0.5290 ± 0.1367 | 0.7303 ± 0.1651* |

*P < 0.05 vs control group

While the effectiveness of 7-week continuous oral administration (total dose 147 mg/kg) of high concentration pioglitazone (3 mg/kg) has been acknowledged (see Biomedicine & Pharmacotherapy 62 (2008) 46-52), it was found from the above that the administration of nanoparticles containing an extremely small amount ($1/130$) of pioglitazone significantly promotes angiogenesis presumed to be due to an endothelial function improving effect.

This application is based on application Nos. 2007-322409 and 2008-125071 filed in Japan, the contents of which are incorporated hereinto by reference.

The invention claimed is:

1. A nanoparticle comprising pioglitazone or a salt thereof and a biocompatible polymer, wherein the biocompatible polymer is a lactic acid-glycolic acid copolymer.

2. The nanoparticle of claim 1, wherein the content of pioglitazone or a salt thereof is 0.1 to 10 wt % as pioglitazone.

3. A pharmaceutical composition comprising the nanoparticle of claim 1 and a pharmacologically acceptable carrier.

4. A stent carrying the nanoparticle of claim 1.

5. A method for the prophylaxis or treatment of an arteriosclerotic disease in a mammal, comprising administering an effective amount of the nanoparticle of claim 1 to the mammal.

6. A method for the prophylaxis or treatment of an arteriosclerotic disease in a mammal, comprising placing the stent of claim 4 in a blood vessel of the mammal.

7. The nanoparticle of claim 1, wherein pioglitazone or a salt thereof is pioglitazone hydrochloride.

8. The pharmaceutical composition of claim 3, wherein pioglitazone or a salt thereof is pioglitazone hydrochloride.

9. The stent of claim 4, wherein pioglitazone or a salt thereof is pioglitazone hydrochloride.

10. The method of claim 5, wherein pioglitazone or a salt thereof is pioglitazone hydrochloride.

11. The method of claim 5, wherein the nanoparticle is intravenously or intraarterially administered to the mammal.

12. The method of claim 6, wherein pioglitazone or a salt thereof is pioglitazone hydrochloride.

* * * * *